United States Patent [19]

Erpenbach et al.

[11] Patent Number: 5,380,929
[45] Date of Patent: Jan. 10, 1995

[54] PROCESS FOR THE PREPARATION OF ACETIC ACID AND ACETIC ANHYDRIDE

[75] Inventors: Heinz Erpenbach, Cologne; Klaus Gehrmann, Erftstadt; Erhard Jägers, Bornheim; Georg Kohl, Hürth, all of Germany

[73] Assignee: Hoechst Aktiengesellschaft, Frankfurt am Main, Germany

[21] Appl. No.: 236,669

[22] Filed: May 2, 1994

Related U.S. Application Data

[63] Continuation of Ser. No. 126,805, Sep. 24, 1993, abandoned, which is a continuation of Ser. No. 373,806, Jun. 29, 1989, abandoned.

[30] Foreign Application Priority Data

Jul. 13, 1988 [DE] Germany ............... 3823645

[51] Int. Cl.$^6$ .................................. C07C 51/12
[52] U.S. Cl. .................... 562/519; 562/890; 562/891
[58] Field of Search ............... 562/519, 890, 891, 517

[56] References Cited

U.S. PATENT DOCUMENTS

| | | | |
|---|---|---|---|
| 3,772,380 | 11/1973 | Paulik et al. | 560/232 |
| 4,046,807 | 9/1977 | Kuckertz | 560/232 |
| 4,110,359 | 8/1978 | Marion | 518/703 |
| 4,333,884 | 6/1982 | Kübbeler et al. | 260/546 |
| 4,430,273 | 2/1984 | Erpenbach et al. | 260/546 |
| 4,549,937 | 10/1985 | Erpenbach et al. | 560/232 |
| 4,559,183 | 12/1985 | Hewlett | 560/232 |
| 4,615,806 | 10/1986 | Hilton | 210/690 |
| 4,664,753 | 5/1987 | Erpenbach et al. | 560/232 |

FOREIGN PATENT DOCUMENTS

| | | |
|---|---|---|
| 1214472 | 11/1986 | Canada . |
| 1234150 | 3/1988 | Canada . |
| 0144936 | 6/1985 | European Pat. Off. . |
| 0173170 | 3/1986 | European Pat. Off. . |
| 0087869 | 7/1986 | European Pat. Off. . |
| 0265140 | 4/1988 | European Pat. Off. . |
| 921938 | 1/1955 | Germany . |
| 2836084A1 | 3/1980 | Germany . |
| 2939839A1 | 4/1981 | Germany . |
| 61-058803 | 3/1986 | Japan . |
| 906008 | 9/1962 | United Kingdom . |

*Primary Examiner*—Arthur C. Prescott
*Attorney, Agent, or Firm*—Connolly & Hutz

[57] ABSTRACT

To prepare acetic acid and acetic anhydride, methanol and methyl acetate are reacted under anhydrous conditions with carbon monoxide in the presence of a catalyst system containing carbonyl complexes of group VIII noble metals, methyl iodide, an alkali metal acetate or iodide, or quaternary organophosphonium or organoammonium acetate or iodide, The hot carbonylation mixture is decompressed, the evaporated components are fed to a first distillation zone, and the catalyst solution which remains is fed back to the reaction zone. In the first distillation zone, the volatile carbonylation products are subjected to fractional distillation; the low-boiling methyl iodide and methyl acetate pass back into the reaction zone, and the bottom product produced is a mixture of acetic acid and acetic anhydride, which is split into the pure components in a second distillation zone and a third distillation zone.

7 Claims, 1 Drawing Sheet

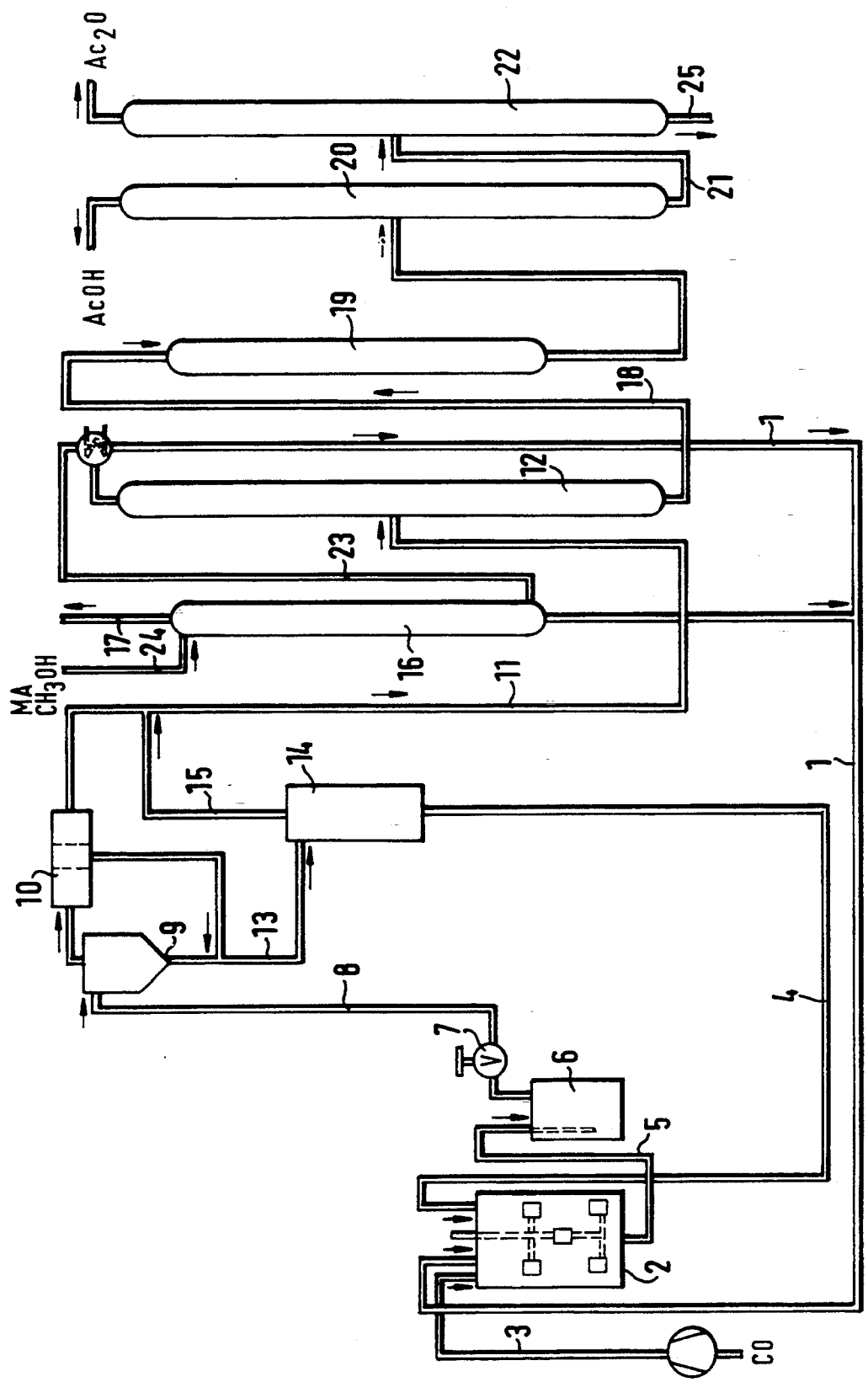

PROCESS FOR THE PREPARATION OF ACETIC ACID AND ACETIC ANHYDRIDE

This application is a continuation, of application Ser. No. 08/126,805 filed on Sep. 24, 1993, which is a continuation, of application Ser. No. 07/373,806 filed on Jun. 29, 1989.

The invention relates to a process for the preparation of acetic acid and acetic anhydride by reacting methanol and methyl acetate with carbon monoxide.

Acetic acid and acetic anhydride are important aliphatic intermediates. The major part is used for the preparation of vinyl acetate and cellulose acetate.

EP-A 87,869 describes a process for the common preparation of acetic acid and acetic anhydride. In this process, methyl acetate or dimethyl ether, water and, if appropriate, methanol, are reacted with carbon monoxide in the presence of a catalyst comprising a noble metal from group VIII of the Periodic Table of the Elements, a bromine or iodine promoter and a copromoter comprising a Lewis base or a non-noble metal, to form a mixture of acetic acid and acetic anhydride, the water content of the mixture employed being at least 5.5% by weight. However, the total amount of water and alcohol should not exceed 85% of the stoichiometric amount of ester and ether.

However, such reaction mixtures which, besides acetic acid and reactive iodine compounds, also contain water are highly corrosive towards most industrial materials, even towards Hastelloy stainless steels, which means that it is necessary to fall back on more expensive materials such as, for example, tantalum.

Surprisingly, the present invention makes it possible to avoid the disadvantages described. In the process of the invention, a) methanol and methyl acetate in the molar ratio 10:1 to 1:10 are reacted under anhydrous conditions with carbon monoxide or mixtures of carbon monoxide and hydrogen in the presence of a catalyst system containing carbonyl complexes of noble metals from group VIII of the Periodic Table of the Elements, methyl iodide and, as promoter, an alkali metal acetate or iodide, or quaternary organophosphonium or organoammonium acetate or iodide, in a reaction zone at temperatures of from 150° to 250° C. and pressures of from 5 to 120 bar;

b) the carbonylation mixture leaving the reaction zone at a temperature of from 150° to 250° C. is decompressed to a pressure of from 1 to 3.5 bar in a vapor-liquid deposition zone, the major part of the volatile components evaporating immediately and, in order to prevent entrainment of liquid drops, being fed via a mist eliminator to a first distillation zone for removal of the low-boiling components; the major part of the still-volatile components is distilled off in a separation zone at a pressure of from 0.05 to 1 bar and a bottom temperature of from 50° to 170° C. from the liquid stream produced in the vapor-liquid deposition zone and in the mist eliminator and is likewise fed to the first distillation zone, and the catalyst solution which remains as the bottom product is fed back to the reaction zone;

c) the volatile carbonylation products are split in the first distillation zone by fractional distillation under atmospheric pressure into a low-boiling component predominantly comprising methyl iodide and methyl acetate, and is fed back into the reaction zone, and the bottom product obtained is a mixture of acetic acid and acetic anhydride;

d) in order to remove traces of iodine-containing compounds, the mixture of acetic acid and acetic anhydride is passed over a carrier containing a silver salt or treated with peracetic acid, and is split into the pure components, acetic acid and acetic anhydride, by fractional distillation in a second distillation zone and a third distillation zone.

In addition, the process of the invention may optionally and preferably have the features that 1) during the fractional distillation in the first distillation zone, an offgas predominantly comprising $CO_2$, CO, $CH_4$ and $N_2$ is withdrawn at the head of the column, freed from residual methyl iodide by washing with the total amount of the starting materials methanol and methyl acetate, and passed to combustion, and the mixture of methanol and methyl acetate is fed to the reaction zone;

2) the catalyst system contains, as additional promoter, a compound of a carbonyl-forming non-noble metal from groups IV to VIII of the Periodic Table of the Elements;

3) the residence times of the starting materials in the reaction zone are from 2 to 50 minutes, depending on the flow rates of the catalyst solution fed back to the reaction zone and of the low-boiling components methyl iodide and methyl acetate and of the starting materials methanol and methyl acetate;

4) the starting material methyl acetate (MA) is replaced partly or fully by dimethyl ether (DME);

5) a noble metal:promoter:methyl iodide:methyl acetate molar ratio of 1:2–100:10–300:10–1000 is maintained in the overall stream fed to the reaction zone at a noble metal concentration of from 0.005 to 0.05 mol/l;

6) the carbonylation mixture leaving the reaction zone flows through a subsequent reactor at 150° to 250° C. and residence times of from 0.5 to 15 minutes in order to convert dissolved carbon monoxide;

7) the distillative separation of the volatile components from the catalyst solution in the separation zone is carried out in the presence of carbon monoxide or mixtures of carbon monoxide and hydrogen;

8) the mixtures of carbon monoxide and hydrogen contain up to 5% by volume of hydrogen; and 9) the mist eliminator contains filter fabrics made from corrosion-resistant substances, preferably glass fibers or stainless steel.

The carbon monoxide employed for the reaction need not necessarily be pure. Relatively small amounts of inert gases, such as carbon dioxide, nitrogen or methane, do not interfere with the carbonylation if the carbon monoxide partial pressure in the reactor is kept constant. A hydrogen content of up to 5% by volume has a positive effect on the catalyst activity, but reduces the selectivity of the process through formation of hydrogenation products, such as, for example, ethylidene diacetate or ethylene glycol diacetate.

As catalyst, any noble metal from group VIII of the Periodic Table (Ru, Rh, Pd, Os, Ir or Pt) can be employed. However, the highest activity is possessed by rhodium. The form of rhodium employed can be any compound which is soluble under the reaction conditions and which form the active noble metal carbonyl complex, for example rhodium chloride, Rh acetate and rhodium carbonyl chloride.

Of the alkali metal iodides employed as promoter salt, lithium iodide has the greatest importance, but sodium iodide or potassium iodide can also be used. The preferred quaternary organophosphonium iodide employed is methyltributylphosphonium iodide, but the use of other phosphonium iodides, such as methyltriphenylphosphonium iodide, tetrabutylphosphonium iodide or dimethyldibutylphosphonium iodide, is also possible. The preferred quaternary organoammonium compound employed is N,N-dimethylimidazolium iodide, N-methylpyridinium iodide, N-methyl-3-picolinium iodide, N-methyl-2,4-lutidinium iodide, N-methyl-3,4-lutidiniumiodide, N-methylquinolinium iodide and others can also be used. The concentration of the promoter salt in the reaction mixture can be between 0.01 and 5 mol/l, advantageously between 0.1 and 1 mol/l.

The non-noble metals from groups IV, V, VI, VII and VIII of the Periodic Table of the Elements which are optionally used as copromoters and form carbonyl complexes are expediently employed in the reaction in a readily soluble form, for example as the acetylacetonate or carbonyl. The concentrations of these copromoters in the reaction mixture are expediently 0.01 to 0.5 mol/l, preferably 0.05 to 0.3 mol/l. Preferred compounds here are those of the metals Ti, Zr, V, Nb, Ta, Cr, Mo, W, Mn, Re, Fe, Co or Ni.

A particular advantage of the process of the invention is that virtually any ratio between the products acetic acid and acetic anhydride can be produced by varying the ratio of the starting materials methanol and methyl acetate, which means that the process can rapidly be adapted to changing requirements.

The process is preferably carried out in the liquid phase at operating pressures between 20 and 80 bar. The carbonylation process can be carried out in either a batch plant or in a continuous plant.

BRIEF DESCRIPTION OF THE DRAWING

The FIGURE in the drawing represents an example of the apparatus in which the disclosed process can be carried out.

The invention is described in greater detail below with reference to the drawing:

The starting materials methyl acetate (MA) and methanol are fed to the reactor 2 via line 24, offgas washer 16 and line 1 together with the low-boiling components methyl iodide and methyl acetate, which are circulated. Carbon monoxide and the catalyst solution, which is circulated, are likewise fed to the reactor, via line 3 and line 4 respectively. While maintaining a constant reaction volume, the reaction products are withdrawn via line 5 into the subsequent reactor 6 to the extent at which the starting materials are supplied, and decompressed via the decompression valve 7 and the line 8 into the vapor-liquid separator 9. The temperature of the starting materials is selected here so that the heat of reaction can be dissipated by heating the starting materials to the reaction temperature of 150° to 250° C. In the vapor-liquid separator 9, the major part of the low-boiling components is evaporated with decompression and utilizing the heat content. After entrained liquid droplets have been removed in the mist eliminator 10, the vapor stream is fed via line 11 to the low-boiling component column 12. The liquid stream produced in the vapor-liquid separator 9 and in the mist eliminator 10 is fed via line 13 to the separation stage 14. Here, further volatile components are removed and likewise fed to the low-boiling component column 12 via lines 15 and 11, while the catalyst solution produced in the separation stage 14 as the bottom product passes back into the reactor 2 via line 4. The low-boiling components methyl iodide and unreacted methyl acetate are separated off at the head of the low-boiling component column 12 under atmospheric pressure and fed back into the reactor 2 via line 1. Via the condenser of the low-boiling component column 12, the offgas is withdrawn via line 23, washed in the offgas washer 16 with the total amount of the starting materials methyl acetate and methanol and thus freed from the methyl iodide which is still being entrained. The offgas ($CO_2$, CO, $CH_4$ and $N_2$) leaves the plant via line 17. The bottom product of the low-boiling component column 12 comprises predominantly acetic acid and acetic anhydride and is passed via line 18 into the column 19 which is packed with a carrier containing a silver salt, for example an ion exchanger resin, where the iodine compounds which are still present in traces in the two products are removed. This can also be carried out at the same point without a carrier containing a silver salt by treating the two products with peracetic acid. The iodine-free products are fractionated in column 20 under reduced pressure. Pure acetic acid is obtained as the head product of column 20. The bottom product is fed via line 21 to column 22, in which pure acetic anhydride is produced at the head under reduced pressure, while the high-boiling components are withdrawn via line 25 as the bottom product.

EXAMPLE 1

The carbonylation is carried out at a temperature of 190° C. under a total pressure of 50 bar. The reactor volume used is 3 liters. The reaction mixture contains the rhodium complex, methyltributylphosphonium iodide, methyl iodide and methyl acetate in the molar ratio 1:18:80:170. The noble metal concentration is 26.5 mmol of Rh/l of reaction mixture.

Per hour, 0.95 kg of methyl acetate (12.8 mol) and 1.9 kg of methanol (59.4 mol) are fed to the reactor 2 via line 24 via the offgas washer 16 and through line 1. At the same time, 2 kg of carbon monoxide (72.4 mol) flow into the reactor through line 3. Furthermore, 4.6 kg of catalyst solution and 11.8 kg of circulated low-boiling components (methyl iodide and methyl acetate) are introduced into the reactor per hour, via line 4 and line 1 respectively. 21.25 kg (=18.6 l) per hour are withdrawn from the reactor via line 5 which gives a mean residence time in the reactor of approximately 10 minutes. The CO still dissolved in the reaction mixture is reacted virtually completely in the subsequent reactor 6 (capacity 1 l) under a reaction pressure of 185° C. The residence time here is somewhat more than 3 minutes. The reaction products are decompressed to 1 bar via the decompression valve 7 to the extent at which the products are introduced into the reactor 2 while maintaining the level, and pass via line 8 into the vapor-liquid separator 9, in which a mean temperature of 95° C. is established. 11.2 kg/h flow in vapor form via the mist eliminator 10, which contains glass fibers and in which catalyst-containing liquid droplets entrained at 90° C. are removed, through line 11 into the low-boiling component column 12. The liquid component from the separator 9 and the mist eliminator 10 pass via line 13 into the separation stage 14, where a further 5.45 kg/h are evaporated under atmospheric pressure and at 145° C. and are likewise fed to the low-boiling component column 12 through lines 15 and 11. The catalyst-containing solution separated off in liquid form in the separation stage 14 is reintroduced into the reactor 2 via line 4.

In the low-boiling component column 12, the low-boiling components methyl iodide and methyl acetate are separated under atmospheric pressure at a bottom temperature of 126° C. and a head temperature of 70° C., and are circulated back into the reaction via line 1. The offgas, which comprises CO, $CO_2$, $CH_4$ and inert gases ($N_2$) is withdrawn via line 23 and freed from methyl iodide, which is entrained in accordance with its partial pressure, in the offgas washer 16 at 0° C. in countercurrent with the starting materials methanol/methyl acetate. The offgas (0.05 kg/h) is fed to combustion via line 17.

The bottom product of the low-boiling component column 12 (4.8 kg/h) which comprises acetic acid, acetic anhydride and high-boiling components, passes via line 18 into column 19, which is packed with a silver-containing ion exchanger, and is purified therein at 50° C. and a residence time of 30 minutes from traces of iodine compounds which are still present.

3.5 kg/h of pure acetic acid (58.3 mol) are subsequently separated off in column 20 under a pressure of 150 mbar at a head temperature of 70° C. and a bottom temperature of 99° C. This corresponds to a yield, based on the methanol employed, of 98.1%.

The bottom product of column 20 is likewise fractionated in column 22, again under a pressure of 150 mbar. At a head temperature of 90° C. and a bottom temperature of 104° C., 1.25 kg/h of pure acetic anhydride (12.25 mol) are produced, which corresponds to a yield of 95.7%, based on the methyl acetate reacted.

As the bottom product from column 22, 0.05 kg/h of high-boiling components is withdrawn via line 25. The yield of acetic acid and acetic anhydride, based on the CO employed, is 97.4%. The reactor performance is 1583 g of acetic acid and acetic anhydride per liter of reaction volume and per hour. The carbonylation performance is 667 g of CO per liter of reactor volume and per hour.

EXAMPLE 2

Under reaction conditions unchanged compared with Example 1, the reactor volume utilized is 4.5 liters. The reaction mixture contains the rhodium complex, methyltributylphosphonium iodide, methyl iodide and dimethyl ether in the molar ratio 1:18:78:152. The noble metal concentration is 27 mmol of rhodium/l of reaction mixture. Per hour, 1.5 kg of dimethyl ether (32.4 mol) and 0.7 kg of methanol (22.5 mol) are fed to the reactor 2 via line 1. In the same time, 2.5 kg of CO (88 mol) flow into the reactor through line 3. Furthermore, 7.1 kg of catalyst solution and 21.2 kg of low-boiling components (methyl iodide and methyl acetate) are introduced per hour into the reactor, via line 4 and line 1 respectively. 33 kg (=28.7 l) are withdrawn from the reactor 2 per hour via line 5, which gives a residence tithe in the reactor of 9.5 minutes. The CO still dissolved in the reaction mixture is reacted virtually completely in the subsequent reactor 6 at a residence time of 2 minutes under reaction pressure at 185° C. The reaction products are decompressed to 1 bar via the decompression valve 7 to the extent at which the products are fed to the reactor 2 while maintaining the level, and pass via line 8 into the vapor-liquid separator 9, in which a mean temperature of 105° C. is established. 17.3 kg/h flow in vapor form through the mist eliminator 10, which contains glass fibers and in which catalyst-containing liquid droplets entrained at 95° C. are removed, through line 11 into the low-boiling component column 12. The liquid component from the separator 9 and the mist eliminator 10 passes via line 13 into the separation stage 14, in which a further 8.6 kg/h are evaporated under a pressure of 150 mbar and at 95° C. while 20 l/h of CO containing 5% by volume of hydrogen are metered in, and are likewise fed to the low-boiling component column 12 through lines 15 and 11. The catalyst-containing solution separated off in liquid form in the separation stage 14 is fed back to the reactor 2 via line 4.

The low-boiling components methyl iodide and methyl acetate are separated off in the low-boiling component column 12 under atmospheric pressure at a bottom temperature of 132° C. and a head temperature of 78° C. and are circulated back into the reaction via line 1. The offgas, which comprises CO, $CO_2$, methane and inert gases ($N_2$), is withdraw via line 23 and freed from methyl iodide, which is entrained in accordance with its partial pressure, in the offgas washer 16 at −20° C. in countercurrent with the starting material methanol. The offgas (0.05 kg/h) is fed to combustion via line 17. The bottom product from the low-boiling component column 12 (4.65 kg/h), which comprises acetic acid, acetic anhydride and high-boiling components, passes via line 18 into column 19 and is treated therein at 120° C. and a mean residence time of 20 minutes through addition of 140 g/h of a 10% strength solution of peracetic acid in acetic acid. 1.32 kg/h of pure acetic acid (22 mol) are subsequently separated off in column 20 under a pressure of 150 mbar at a head temperature of 70° C. and a bottom temperature of 99° C. This corresponds to a yield, based on the methanol employed, of 97.8%. The bottom product from column 20 is fractionated in column 22, again under a pressure of 150 mbar. 3.28 kg/h of pure acetic anhydride (32.15 mol) are produced at a head temperature of 90° C. and a bottom temperature of 104° C., which corresponds to a yield of 99.2%, based on the dimethyl ether employed. As the bottom product from column 22, 0.05 kg/h of high-boiling components are removed via line 25. The yield of acetic acid and acetic anhydride, based on the CO employed, is 98%. The reactor performance is 1022 g of acetic acid and acetic anhydride per liter of reactor volume and per hour. The carbonylation performance is 556 g of CO per liter of reactor volume and per hour.

| Example | 3 | 4 | 5 | 6 | 7 | 8 | 9 | 10 |
|---|---|---|---|---|---|---|---|---|
| Input: | | | | | | | | |
| mol $CH_3OH$/h | 12 | 28 | 35 | 48 | 6 | 36 | 42 | 28 |
| mol MA/h | 62 | 42 | 35 | 26 | 48 | 29(DME) | 25 | 32 |
| mol CO/h | 75 | 70 | 70.5 | 74.5 | 55 | 95 | 67.5 | 61 (+3$H_2$) |
| mmol Rh/l | 8 | 30 | 25 | 27.5 | 28 | 30 | 25 | 30 |
| Reactor volume, l Rv | 4.5 | 4.5 | 3.0 | 3.0 | 3.0 | 4.5 | 4.5 | 3.0 |

-continued

| Example | 3 | 4 | 5 | 6 | 7 | 8 | 9 | 10 |
|---|---|---|---|---|---|---|---|---|
| Residence time in reactor, min | 12 | 20 | 10 | 9 | 12 | 10 | 10 | 10 |
| Molar ratios: | | | | | | | | |
| Rh | 1 | 1 | 1 | 1 | 1 | 1 | 1 | 1 |
| : | | | | | | | | |
| promoter | Li acetate | N,N-dimethylimidazol- ium iodide | | methyltributylphosphonium iodide | | | | |
| | 26 | 18 | 18 | 18 | 18 | 18 | 18 | 18 |
| | — | — | zirconim acetyl- acetonate | vanadim hexa- carbonyl | chromium hexa- carbonyl | rhenium deca- carbonyl | Ni acetate | — |
| | | | 2 | 2 | 2 | 2 | 2 | |
| $CH_3I$ | 230 | 80 | 80 | 82 | 78 | 80 | 86 | 79 |
| : | | | | | | | | |
| MA | 580 | 180 | 180 | 175 | 185 | 160 | 150 | 150 |
| Yield of AcOH, based on the $CH_3OH$ employed | 98.5 | 99.0 | 98.7 | 96.8 | 98.8 | 98.7 | 99.0 | 99.8 |
| Yield of $Ac_2O$, based on the conversion of MA | 98.2 | 97.8 | 98.4 | 97.2 | 98.0 | 98.2(DME) | 97.8 | 99.8 |
| Yield of AcOH + $Ac_2O$, based on the CO employed | 96.9 | 98.3 | 97.7 | 96.4 | 96.2 | 97.4 | 97.9 | 96.6 |
| Performance | | | | | | | | |
| g AcOH + $Ac_2O$/l Rv × h | 1535 | 1300 | 1862 | 1789 | 1718 | 1119 | 1109 | 1612 |
| g CO/l Rv × h | 467 | 435 | 658 | 695 | 513 | 591 | 420 | 569 |

We claim:

1. In a process for the preparation of acetic acid and acetic anhydride by reacting methanol and at least one substance selected from methyl acetate and dimethyl ether with carbon monoxide or mixtures of carbon monoxide and hydrogen in the presence of a catalyst system consisting essentially of carbonyl complexes of noble metals from group VIII of the Periodic Table of the Elements, methyl iodide and, as promoter, a quaternary organophosphonium or organoammonium acetate or iodide, in a reaction zone, the improvement which comprises a) methanol and methyl acetate or dimethyl ether in the molar ratio 10:1 and 1:10 are reacted under anhydrous conditions at temperatures of from 150° to 250° C. and pressures of from 5 to 120 bar;

b) the carbonylation mixture leaving the reaction zone at a temperature of from 150° to 250° C. is decompressed to a pressure of from 1 to 3.5 bar in a vapor-liquid deposition zone, the major part of the volatile components evaporating immediately and, in order to prevent entrainment of liquid drops, being fed via a mist eliminating zone to a first distillation zone for removal of the low-boiling components; the major part of the still volatile components is distilled off in a separation zone at a pressure of from 0.05 to 1 bar and a bottom temperature of from 50° to 170° C. from the liquid stream produced in the vapor-liquid deposition zone and in the mist eliminating zone and is likewise fed to the first distillation zone, and the catalyst solution which remains as the bottom product is fed back to the reaction zone;

c) during fractional distillation in the first distillation zone, an offgas, predominantly comprising $CO_2$, CO, $CH_4$ and $N_2$, is withdrawn at the head of the column, freed from residual methyl iodide by washing with the total amount of the starting materials methanol and methyl acetate, and passed to combustion, and the mixture of methanol and methyl acetate is fed to the reaction zone;

d) the volatile carbonylation products are split in the first distillation zone by fractional distillation under atmospheric pressure into a low-boiling component predominantly comprising methyl iodide and methyl acetate, and is fed back into the reaction zone, and the bottom product obtained is a mixture of acetic acid and acetic anhydride;

e) in order to remove traces of iodide-containing compounds, the mixture of acetic acid and acetic anhydride is passed over a carrier containing a silver salt or treated with peracetic acid, and is split into the pure components, acetic acid and acetic anhydride, by fractional distillation in a second distillation zone and a third distillation zone;

f) the residence times of the starting materials in the reaction zone are from 2 to 50 minutes, depending on the flow rates of the catalyst solution fed back to the reaction zone and of the low-boiling components methyl iodide and methyl acetate and of the starting materials methanol and methyl acetate.

2. A process as claimed in claim 1, wherein a noble metal:promoter:methyl iodide:methyl acetate molar ratio of 1:(2 to 100): (10 to 300):(10 to 1000) is maintained in the overall stream fed to the reaction zone at a noble metal concentration of from 0.005 to 0.05 mol/l.

3. A process as claimed in claim 1, wherein the carbonylation mixture leaving the reaction zone flows through a subsequent reactor at 150° to 250° C. and residence times of from 0.5 to 15 minutes in order to convert dissolved carbon monoxide.

4. A process as claimed in claim 1, wherein the distillative separation of the volatile components from the catalyst solution in the separation zone is carried out in the presence of carbon monoxide or mixtures of carbon monoxide and hydrogen.

5. A process as claimed in claim 1, wherein the mixtures of carbon monoxide and hydrogen contain up to 5% by volume of hydrogen.

6. A process as claimed in claim 1, wherein the mist eliminating zone contains filtering means made from corrosion-resistant substances.

7. In a process for the preparation of acetic acid and acetic anhydride by reacting methanol and at least one substance selected from methyl acetate and dimethyl ether with carbon monoxide or mixtures of carbon monoxide and hydrogen in the presence of a catalyst system consisting essentially of carbonyl complexes of noble metals from group VIII of the Periodic Table of the Elements, methyl iodide and, as promoter, a quaternary organophosphonium or organoammonium acetate of iodide, in a reaction zone, the improvement which comprises a) methanol and methyl acetate or dimethyl ether in the molar ratio 10:1 and 1:10 are reacted under anhydrous conditions in the presence of said catalyst system which additionally includes as promoter a compound of a carbonyl-forming non-noble metal from groups IV to VIII of the Periodic Table of the Elements, at temperatures of from 150° to 250° C. and pressures of from 5 to 120 bar;

b) the carbonylation mixture leaving the reaction zone at a temperature of from 150° to 250° C. is decompressed to a pressure of from 1 to 3.5 bar in a vapor-liquid deposition zone, the major part of the volatile components evaporating immediately and, in order to prevent entrainment of liquid drops, being fed via a mist eliminating zone to a first distillation zone for removal of the low-boiling components; the major part of the still volatile components is distilled off in a separation zone at a pressure of from 0.05 to 1 bar and a bottom temperature of from 50° to 170° C. from the liquid stream produced in the vapor-liquid deposition zone and in the mist eliminating zone and is likewise fed to the first distillation zone, and the catalyst solution which remains as the bottom product is fed back to the reaction zone;

c) during fractional distillation in the first distillation zone, an offgas, predominantly comprising $CO_2$, CO, $CH_4$ and $N_2$, is withdrawn at the head of the column, freed from residual methyl iodide by washing with the total amount of the starting materials methanol and methyl acetate, and passed to combustion, and the mixture of methanol and methyl acetate is fed to the reaction zone;

d) the volatile carbonylation products are split in the first distillation zone by fractional distillation under atmospheric pressure into a low-boiling component predominantly comprising methyl iodide and methyl acetate, and is fed back into the reaction zone, and the bottom product obtained is a mixture of acetic acid and acetic anhydride;

e) in order to remove traces of iodide-containing compounds, the mixture of acetic acid and acetic anhydride is passed over a carrier containing a silver salt or treated with peracetic acid, and is split into the pure components, acetic acid and acetic anhydride, by fractional distillation in a second distillation zone and a third distillation zone;

f) the residence times of the starting materials in the reaction zone are from 2 to 50 minutes, depending on the flow rates of the catalyst solution fed back to the reaction zone and of the low-boiling components methyl iodide and methyl acetate and of the starting materials methanol and methyl acetate.

* * * * *